(12) United States Patent
Lee et al.

(10) Patent No.: US 6,413,494 B1
(45) Date of Patent: Jul. 2, 2002

(54) COMPOSITION AND PHARMACEUTICAL DOSAGE FORM FOR COLONIC DRUG DELIVERY USING POLYSACCHARIDES

(75) Inventors: Seung Seo Lee; Chang Baeg Lim; Chaul Min Pai; Sujung Lee; In Park; Moon Gun Seo; Heenam Park, all of Taejon-si (KR)

(73) Assignee: Samyang Corporation (KR)

( * ) Notice: Subject to any disclaimer, the term of this patent is extended or adjusted under 35 U.S.C. 154(b) by 0 days.

(21) Appl. No.: 09/318,579

(22) Filed: May 25, 1999

(30) Foreign Application Priority Data

Jul. 23, 1998 (KR) .............................. 98-29740
Apr. 23, 1999 (KR) ........................... 99-14665

(51) Int. Cl.⁷ ...................... A61K 49/00; A61K 9/00; A61K 31/715; A61K 47/36
(52) U.S. Cl. ...................... 424/9.1; 127/29; 424/451; 424/463; 424/464; 424/474; 424/479; 424/488; 424/493; 424/499; 514/54; 514/777; 514/960; 514/962; 536/1.11; 536/2; 536/123.1; 536/124
(58) Field of Search .................. 424/461, 463, 424/474, 479, 481, 485, 488, 493, 496, 499, 500, 9.1, 451, 464; 514/54, 777, 960, 962; 536/1.11, 2, 123.1, 124; 127/29

(56) References Cited

U.S. PATENT DOCUMENTS 5,422,121 A    6/1995   Lehmann et al. ........... 424/464
5,562,924 A  * 10/1996  Perrier et al. ............... 424/499

FOREIGN PATENT DOCUMENTS

WO           97/30092    *  8/1997

OTHER PUBLICATIONS

Da Silva et al., Journal of Food Science (1992), vol. 57, No. 2, pp. 443–448.*

STN/CAS online, file FSTA, Acc. No. 74(07):P1042, (Qureshi et al., Science and Industry, Pakistan (1972) ((3/4), pp. 211–215), Abstract.*

* cited by examiner

Primary Examiner—Jose' G. Dees
Assistant Examiner—Frank Choi
(74) Attorney, Agent, or Firm—Gates & Cooper LLP (57) ABSTRACT

A colonic drug delivery composition contains a first polysaccharide and a second polysaccharide wherein both polysaccharide are degradable by colonic enzymes and are mixed at a environmental pH of about 7 or above, without use of a cross-linking agent. A colon selective pharmaceutical composition and dosage form for oral delivery of a drug, diagnostic reagent, or mixture thereof includes the drug, diagnostic reagent, or mixture thereof in contact with the polysaccharide composition. A method of preparing such a colonic drug delivery composition and the colon selective pharmaceutical composition and dosage from are also disclosed.

32 Claims, 2 Drawing Sheets

COMPOSITION AND PHARMACEUTICAL DOSAGE FORM FOR COLONIC DRUG DELIVERY USING POLYSACCHARIDES

This application claims the benefit of Korean patent application numbers 98-29740, filed Jul. 23, 1998, and 99-14665, filed Apr. 23, 1999. The entire contents of each of these priority applications are hereby incorporated by reference into this application.

In addition, throughout this application, various publications are referenced. The entire contents of these publications are hereby incorporated by reference into this application in order to more fully describe the state of the art to which it pertains.

FIELD OF THE INVENTION

This invention relates to a composition and oral pharmaceutical dosage form for selective delivery of drugs to the colon. More particularly, the invention relates to compositions and oral pharmaceutical dosage forms for release of biologically active ingredients in the colon while avoiding or minimizing release into the upper gastrointestinal tract, such the stomach and small intestine.

BACKGROUND OF THE INVENTION

Numerous drug entities based on oral delivery have been successfully commercialized, but many others are not readily available by oral administration, which are incompatible with the physical and/or chemical environments of the upper GI tract and/or demonstrate poor uptake in the upper GI tract. Due to the lack of digestive enzymes, colon is considered a suitable site for the absorption of various drugs. However, colon drug delivery is hardly achieved in that the oral dosage form should pass through the stomach and small intestine, where many drugs are deactivated by their digestive materials. Ideally, a colon specific drug delivery system is designed such that it remains intact in stomach and small intestine but releases encapsulated drugs only in colon. CSDS system is useful in administering a drug that is an irritant to the upper GI tract, such as non-steroidal anti-inflammatory agents, or drugs that are degraded by gastric juice or an enzyme present in the upper GI tract, such as peptide or protein. Further, the colonic drug delivery system allows local, direct treatment of colonic disease, e.g., ulcerative colitis, Crohn's disease, or colon cancer, thus reducing the dosage of the drugs and minimizing undesirable or harmful side effects. Similarly, colonic drug delivery is useful for administering drugs, e.g. non-steroidal anti-inflammatory drugs (NSAIDS), which are irritants to the mucosa of the upper gastrointestinal tract such as the stomach or small intestine. Recently, it is believed that colonic drug delivery systems maintain the efficacy of drugs for a longer time and increase the bioavailability of the drugs as compared to other oral routes of administration. As the colon has a longer retention time, drug absorption is prolonged, and total bioavailability is increased. A. Sintov et al., 143 Int. J. Pharma. 101–106 (1996).

Although colon is attracting interest as a site for delivering several drugs such as unstable drugs in upper GI tract or poorly-absorbed drugs, it is very difficult to diver the drug into colon effectively. In order to deliver a drug to the colon selectively, a composition generally should meet the following requirements: (1) the composition is not degraded or disintegrated in the upper GI tract; (2) the composition does not release the loaded drug in the upper GI tract; (3) the composition releases the drug effectively at the target site, the colon, more particularly the ascending colon; and (4) the composition is easy to formulate in a form suitable for loading the drug. Further, the composition preferably can be easily processed for manufacture.

Several approaches have been used in developing colon-specific drug delivery systems. One is based on the different pH of each compartment of the gastrointestinal tract, with the pH of the proximal GI tract being lower than that of the distal GI tract. Thus, polymers that are insoluble at low pH and soluble at higher pH have been used to deliver drugs to the distal GI tract Another approach is based on the fact that transit time through the stomach is approximately 2 hours, whereas transit time through the small intestine is approximately 4–6 hours. Thus, in this approach, the delivery system is designed to withhold the release of the drugs for about 6–8 hours from the time of administration.

Moreover, it is well known that enzymes capable of reducing azo bonds or hydrolyzing glycosidic bonds, which are not degraded in the stomach and small intestine, are present in the colon. Thus, many approaches to colonic drug delivery use azo bond-containing polymers (azo polymers) or glycosidic bond-containing materials. The glycosidic bond-containing polymers include disaccharides, oligosaccharides, and polysaccharides.

For example, U.S. Pat. No. 5,482,718; U.S. Pat. No. 4,627,851; U.S. Pat. No. 4,693,895; U.S. Pat. No. 4,705,515; U.S. Pat. No. 4,904,474; EP 621 032 A1; JP 34929/1991A; U.S. Pat. No. 5,536,507; EP 453 001 A1; U.S. Pat. No. 5,171,580; and EP 572 942 A2 disclose time dependent drug delivery system. They are designed to prevent drug release for a period of time expected to be sufficient for the composition to pass through the upper gastrointestinal tract. Further, U.S. Pat. No. 5,401,512; U.S. Pat. No. 5,541, 170;and WO 95/11024 describe drug compositions for selectively releasing the drug in the colon by way of exploiting the difference in pH between the colon and other parts of the GI tract.

The above-mentioned compositions, however, are not effective in delivering the drug to the colon. The pH in the terminal ileum and colon is higher than other region of the GI tract and thus composition which disintegrate at high pH level have the potential for site specific delivery into this region. However, because the pH is higher in the terminal ileum region than in the colon, and the dosage forms are often delayed at the ileo-cecal junction, the dosage forms based on pH dependent system are often disintegrate in the terminal ileum instead of disintegrate in colon. Further, the colon specific delivery based on GI transit time-dependent system is hardly to be achieved. The transit time in the upper gastrointestinal tract tends to be highly variable among individuals.

Many approaches to colonic drug delivery use azo bond or glycosidic bond-containing drugs, i.e. prodrug and have been successfully come into the market. The prodrug that is activated only in the colon requires covalent bonding between the drug molecule and carrier molecules such that the covalent bonds are broken only by enzymes produced by colonic bacteria. WO 84/04041, WO 93/22334; A. D. McLeod et al., 83 J. Pharm. Sci. 1284–1288(1994); D. R. Friend et al., 27 J. Med. Chem. 261–266 (1984); B. Haeberlin et al., 10 Pharm. Res. 1553–1562 (1993); D. R Friend et al. 28 J. Med. Chem. 51–57 (1985); DR Friend, 5 S.T.P. Pharma Sci. 70–76 (1995); J. P. Brown et al., 26 J. Med. Chem. 1300–1307(1983).

It is well known that enzymes capable of breaking an azo, disulphide bonds and glycosidic bond are present in the colon, but not in the upper GI tract. WO 91/16057 and EP 398 472 A2 disclose compositions containing an azo polymer having azo bonds as a colonic drug delivery system. Although the composition is relatively stable in the upper gastrointestinal tract, the dosage form coated by azo polymer does not showed colon specificity effectively. Azo reductase produced by colonic microflora cannot easily reach the azo bond of azo-polymers due to the hydrophobic nature of the azo-polymer, thus resulting in slow degradation in the colon of the composition containing the azo polymer. P. Y. Yeh et al., 196 Macromol. Chem. Phys. 2183–2202 (1995).

A number of delivery systems based on polysaccharides which are selectively degraded by colonic enzyme have been reported, since polysaccharides are natural polymers with proven final toxicity U.S. Pat. No. 5,505,966 discloses a pharmaceutical composition containing calcium pectinate as a major component and a filler such as pectin, dextran, avicel, or mixture thereof. U.S. Pat. No. 5,525,634 discloses a pharmaceutical composition containing a synthetic or natural polymer that is degradable by a colonic enzyme, herein calcium pectinate is disclosed as an example of a natural polymer.

In U.S. Pat. No. 5,505,966, the calcium pectinate composition is used in the form of a coacervate pellet. It is believed that calcium pectinate, which is insoluble in water, is converted to a water-soluble matrix by sodium ions or potassium ions present in the digestion solution of upper GI. Therefore, the system mainly depends on transit time of upper GI, thus the pellets often disintegrate and release the drug in upper GI.

U.S. Pat. No. 5,525,634 suggests a compressed tablet formulation that is prepared by pulverizing and compressing a pharmaceutical composition containing a drug and calcium pectinate. In the composition, the strength of compression largely affects the system disintegration through the GI tract. The weak compressed tablet disintegrates easily in the upper gastrointestinal tract by converting to a water-soluble matrix, which caused by sodium ions or potassium ions present in the digestion solution of upper GI. Further, the strongly compressed tablet is hardly disintegrated in colon. Therefore, the compositions disclosed in both U.S. Pat. No. 5,505,966 and U.S. Pat. No. 5,525,634 is highly dependent on the system swelling and on the transit time through the upper gastrointestinal tract, and not on unique characteristics of the composition.

To solve the above problem, Adkin, D. A. et al. suggests the addition of guar gum or pectin as a binder of calcium pectinate compressed tablets and coating them with enteric material. Adkin, D. A. et al. 14 Pharm. Res. 103–107 (1997). Guar gum or pectin is used as a binder for preventing easy disintegration in upper GI and resulted in sustained release effect in colon. Enteric coating is also used for preventing the rapid swelling and disintegration in upper GI. However this system also present slow release of drug in colon and is highly dependent on the enteric coating thickness and on the transit time through the upper gastrointestinal tract, and not on unique characteristics of the composition.

U.S. Pat. No. 4,432,966 discloses a composition comprising microcrystalline cellulose and ethyl cellulose; EP 627 173 A1 describes a cellulose composition; WO 95/35100 discloses a starch capsule and a composition comprising an enteric coating; U.S. Pat. No. 5,422,121 discloses a composition comprising a guar gum or locust bean gum blended with a film forming material. The latter composition is formulated by using polysaccharide with the film forming materials. Generally polysaccharides have the hydrophilic moiety and have a difficulty in fabricating the coating film in the coated dosage form due to its physical properties. In addition, the polysaccharide films and matrix fabricated by compression method, they are easily disintegrated in upper GI. Therefore, polysaccharides are mixed with the more hydrophobic film-forming material in the above-mentioned composition. Although the blend of polysaccharide and film forming material shows the improved film forming properties, a hydrophobic film-forming material generally has the lower swelling ratio than that of a polysaccharide. Due to the swelling ratio difference, the coated film comprising a polysaccharide and a film forming material is often phase-separated and bring a crack during passage through the stomach and small intestine. In addition, the using hydrophobic film forming material bring the undesirable result that disintegration of dosage form by colonic enzyme is delayed due to the hydrophobic nature of the mixed polymer, thus resulting in slow degradation in the colon of the composition. It may be happened that colonic enzyme from microflora cannot easily reach the polysaccharide due to the hydrophobic nature of the mixed polymer. Accordingly, the drug is often released in the upper gastrointestinal tract, or it is so slow drug release that the system fails to show colon specific drug delivery. In view of the foregoing, it will be appreciated that providing a polysaccharide-based composition for controlled drug delivery in the colon would be a significant advancement in the art.

BRIEF SUMMARY OF THE INVENTION

An object of the present invention is to provide a composition and pharmaceutical dosage form for delivering a drug, wherein such dosage form is orally-administered for specifically delivering the drug to the colon of a subject in need thereof.

Another object of the invention is to provide a composition and pharmaceutical dosage form for colonic drug delivery that is not degraded or disintegrated in the upper GI tract.

Still another object of the invention is to provide a composition and pharmaceutical dosage form for delivering an orally-administered drug is that is inactivated in the upper GI tract, wherein the dosage form is in a form that passes through the upper GI tract and then releases the drug in the colon of a human subject in need thereof.

Yet another object of the invention is to provide a composition and pharmaceutical dosage form for colonic drug delivery that releases the drug rapidly and effectively at the target site, the colon, and minimizes adverse systemic effects to a subject being treated.

Another object of the invention is to provide a composition and pharmaceutical dosage form for colonic drug delivery that is easy to formulate in a form suitable for loading the drug to be delivered.

Still another object of the invention is to provide a method for treating a subject through oral administration of a pharmaceutical dosage form and composition that achieves the foregoing objects of this invention.

Yet another object of the invention is to provide a process for preparing a pharmaceutical dosage form and composition that achieves the forgoing objects of this invention.

One aspect of this invention is a composition and pharmaceutical dosage form designed for delivering an orally administered drug to the colon. The composition passes through the upper GI tract without releasing the drug, but the drug is rapidly and effectively released at the target site in the colon, more especially in the ascending colon, minimizing adverse systemic effects to a human subject being treated. The composition comprises a mixture, prepared at a pH of about 7 or above, without use of a cross-linking agent, of a galactomannan and a polysaccharide, preferably pectin, selected from the group consisting of pectin, derivatives of pectin, and mixtures thereof. The composition forms a strong elastic gel that is not appreciably dissolved or disintegrated in gastric or intestinal fluids, thus protecting drugs from being released in the upper GI tract. When the composition arrives in the colon, the composition is easily degraded by synergic effect of pectinolytic enzymes and glactomannanase, thus releasing drugs rapidly in the colon. The ratio of the two polysaccharides determines the rate of enzymatic degradation of the composition and disintegration of dosage form through GI tract, which in turn enables the composition to release the drug site specifically in the colon. More particularly, the ratio and coating thickness of the two Another aspect of this invention provides a colon specific composition and a pharmaceutical dosage form comprising the inventive colonic drug delivery composition and a biologically active substance without additional enteric coating and an independence to individual variance such as pH and transit time. The composition and dosage form of this invention can be in form of a coating material, hard capsule shell material, or matrix.

DETAILED DESCRIPTION OF THE INVENTION

Before the present composition and method for colonic drug delivery are disclosed and described, it is to be understood that this invention is not limited to the particular configurations, process steps, and materials disclosed herein as such configurations, process steps, and materials may vary somewhat. It is also to be understood that terminology employed herein is used for the purpose of describing particular embodiments only and is not intended to be limiting since the scope of the present invention will be limited only by the appended claims and equivalents thereof.

In must be noted that, as used in this specification and the appended claims, the singular forms "a," "an," and "the" include plural referents unless the context clearly dictates otherwise. Thus, for example, reference to a composition containing "a galactomannan" includes a mixture of one or more galactomannans, reference to "a pectin salt" includes reference to one or more of such pectin salts, and reference to "a coating" includes reference one or more of such coatings.

In describing and claiming the present invention, the following terminology will be used in accordance with the definitions set out herein.

As used herein, "colon-specific drug delivery system" and similar terms mean devices and methods for oral administration that release biologically active ingredients in the colon without substantial release into the upper gastrointestinal tract, e.g. stomach and intestine.

As used herein, the term "drug" or "pharmacologically active agent" or any other similar term means any chemical or biological material or compound suitable for administration by the methods previously known in the art and/or by the methods taught in the present invention, that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may be systemic. This invention is not drawn to novel drugs or to new classes of active agents. Rather it is limited to the mode of delivery of agents of drugs that exist in the state of the art or that may later be established as active agents and that are suitable for delivery by the present invention. Such substances include broad classes of compounds normally delivered into the body. In general, this includes but is not limited to: antiinfectives such as antibiotics and antiviral agents; analgesics and analgesic combinations; anorexics; helminthics; antiarthritics; antiasthmatic agents; anticonvulsants; antidepressants; antidiabetic agents; antidiarrheals; antihistamines; antiinflammatory agents; antimigraine preparations; antinauseants ;antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators; including general coronary, peripheral and cerebral; central nervous system stimulants; vasoconstrictors; cough and cold preparations including decongestants; hormones such as estradiol and other steroids, including corticosteroids; hypnotics; immunosuppressives; muscle relaxants; parasympatholytics; psychostimulants; sedatives; and tranquilizers; probiotics. By the method of the present invention, both ionized and nonionized drugs may be delivered, as can drugs of either high or low molecular weight.

As used herein, "nutrient" means a substance that affects the nutritive or metabolic processes of the body. Nutrients include essential nutrients, i.e. those nutrients such as proteins, minerals, carbohydrates, fats, and vitamins necessary for growth, normal functioning, and maintaining life, and secondary nutrients, i.e. substances that stimulate the intestinal microflora to synthesize other nutrients.

As used herein, "diagnostic reagent" means a substance used to produce a chemical reaction so as to detect or measure another substance.

As used herein, "simulated intestinal fluid" or "SIF" means a composition prepared by dissolving 6.8 g of monobasic potassium phosphate in 250 ml of water, then adding 190 ml of 0.2 N NaOH, 400 ml of water and 10 g of pancreatin, and finally adding 0.2 N NaOH to adjust the pH to 7.5, and then diluting with water to 1000 ml.

As used herein, 'simulated gastric fluid' or 'SGF' means a composition prepared by dissolving 2 g of NaCl and 3.2 g pepsin in 7 ml of HCl, and then adding water to 1000 ml. The resulting fluid has a pH of about 1.2.

As used herein, 'derivatives of pectin' and similar terms includes cation salts of pectin such as sodium pectinate, potassium pectinate, and ammonium pectinate, and the like.

As used herein, 'effective amount' means an amount of a drug or pharmacologically active agent that is nontoxic but sufficient to provide the desired local or systemic effect and performance at a reasonable benefit/risk ratio attending any medical treatment. An effective amount of a nutrient is an amount sufficient to provide a selected nutritive benefit. An effective amount of a diagnostic reagent is an amount sufficient to be efficacious in a selected diagnostic test or assay.

The present invention relates to a colonic drug delivery composition comprising a mixture of (a) a polysaccharide selected from the group consisting of pectin, derivatives of pectin, and mixtures thereof, and (b) galactomannan. The mixture is made by combining the ingredients in an aqueous medium at a pH of about 7 or above.

In a preferred embodiment of the invention, the composition comprises (a) pectin or a derivative of pectin or a mixture thereof and (b) galactomannan. The composition is prepared at a pH of about 7 or above. The ratio of ingredients is limited only by functionality. Preferably, however, the composition has a polysaccharide: galactomannan weight ratio of about 50:50 to about 99.9:0.01, more specifically, about 2:1 to about 5:1. A coating prepared with the instantly claimed composition will generally have a mass to area ratio in the range of about 1–100 mg/cm$^2$, and preferably about 1–40 mg/cm$^2$. A hard capsule shell will generally have a thickness of about 1–100 $\mu$m, preferably 1–40 $\mu$m.

A key feature of this invention is based on a change in the properties of a mixture of these two polysaccharides, which is degradable in the colon by colonic bacterial enzymes, as compared to either polysaccharide alone. When pectin or galactomannan (such as guar gum or locust bean gum) is used alone as a drug carrier, e.g., coating material, the coating is easily dissolved and/or disintegrated in simulated gastric fluid (SGF) and simulated intestinal fluid (SIF). However, a mixture of these two polysaccharides prepared at a pH of about 7 or above produces a strong, elastic, and insoluble gel that is not dissolved or disintegrated in the simulated gastric and intestinal fluids, thus protecting drugs coated with the mixture from being released in the upper GI tract. On the other hand, under conditions encountered in the colon, the coating is degraded by pectinolytic enzymes and galactomannanase, thus disintegrating the dosage form and rapidly releasing the drugs. When the coating is prepared at below pH 7, such coating is easily disintegrated and dissolved in the upper GI tract.

Pectin and galactomannan are both degradable by colonic bacterial enzymes. When the mixture of pectin and galactomannan arrives in the colon, it is rapidly degraded by the synergic action of colonic bacterial enzymes. Accordingly, the composition of the present invention can prevent the drug deactivation in upper GI and also produces the burst-like drug release pattern in ascending colon, which is preferred to treat local colon disease such as ulcerative colitis, Crohn's disease. Thus, the composition of the present invention can be used advantageously for specific drug delivery in the colon as compared to known drug delivery systems.

The pH at which the mixture is prepared is a determining factor of the properties of the composition. As shown by experimental data presented herein, films of such mixtures prepared at a pH of about 7 or above were stronger, more elastic and less soluble than films cast from mixtures prepared at a pH below 7. In addition, all films cast with the mixtures prepared at a pH below 7 were easily dissolved in SIF, while films cast from mixtures prepared at a pH of about 7 or above were not extensively dissolved or not dissolved at all in SIF. Either pectin or galactomannan is soluble in aqueous media. Below pH 7, there is no binding force between pectin and galactomannan, whereas, at about pH 7 or above, it is likely that pectin and galactomannan interact each other to form a specific complex gel. Galactomannan is a non-gelling polysaccharide but it can be gelled synergically when mixed with some polysaccharides. Proposed binding forces are synergic action of hydrogen bonding, hydrophobic force and the formation of interjunction zone. The conformational change of polysaccharide chains at pH 7 or above results in the strong interaction. Synergic gellation and interaction of galactomannan and polysaccharides are referred to in C. M. D. Iain, et al., 31 Adv. Carbohydrate. Chem. Biochem. 241–312(1975).

The ratio of the two polysaccharides determines the rate of enzymatic degradation of the composition and dosage disintegration through GI tract, which in turn enables the composition to release the drug site specifically in the colon. More particularly, the ratio of the two polysaccharides enables the composition to release the drug more specifically in the colon such as the ascending, transverse, descending colon. Between the two polysaccharides, the more galactomannan(e.g. guar gum) there is, the less soluble in SIF and the less degradable by colonic enzymes. By increasing the proportion of galactomannans, the composition releases the drug at a site further on than the ascending colon, e.g. the transverse or descending colon. In addition, by changing the dimensions of the dosage form, the site where drugs are released can be controlled. The thickness of a coating or the diameter of a matrix formulation which drug is incorporated can be selected to achieve site specificity within the colon. Thus, the ratio of polysaccharides and the dimensions of the composition are important factors for determining the site of drug release in the colon. By manipulation of these factors in the manufacture of dosage forms according to the present invention, drug delivery can be selectively targeted to the ascending colon or more distally to the transverse or descending colon.

Another improvement of the present invention is that the composition can be used in many different types of dosage forms. The composition can be used as a coating material for tablets, soft capsules, granules, seeds, and the like. Further, it can be used advantageously in hard capsules and matrix pellets.

The composition can be used to deliver a wide range of biologically active ingredients. For example, topically acting drugs such as those for IBD, Crohn's disease, laxatives and colon cancer; systemically acting drugs such as peptide or protein drugs, calcium antagonists, antiasthmatics, hypoglycemic agents, antirheumatic, and the like can be loaded and delivered to the colon with the composition of the present invention. Likewise, nutrients can be loaded and delivered into the colon for a better absorption. Further, pharmaceutically acceptable excipients may be included in the composition.

Because both the pectin and galactomannan components of the composition of the present invention are specifically degraded in the colon, there is a burst of drug release in the colon due to the synergic effect of the colonic enzymatic activities. Compared to the instant invention, previously known dosage forms are much slower and gradual with respect to disintegration, dissolution, or drug release in the colon. The synergic effect of the enzymatic activities is referred to in T Ooya et al., 25 Proc. Int'l Symp. Control. Rel. Bioact. Mater. 731–732(1998).

As stated above, the composition of the present invention can be used as a coating material, hard capsule shell material, or matrix.

Illustrative examples of drugs that can be used in the composition and the dosage form of the invention include: mesalamine, balsalazide, olsalazine, ibuprofen, prednisolone, dexamethasone, budesonide, beclomethasone, flucticasone, tioxocortal, hydrocortisone, metronidazole, cyclosporin, methotrexate, domperidone, 5-fluorouracil, bisacodyl, senna, insulin, vasopressin, growth hormones, colony stimulating factors, calcitonin, immunoglobulin, glibenclimide, diltiazem, verapamil, nifedipine, captopril, benazepril, enalapril, theophylline, naproxen, diclofenac, acyclovir, omeprazole, lovastatin, alendronate, desmopressin, metformin, metoprolol, cisapride, tacrine, mixtures thereof and probiotics. Also, the pharmaceutical composition of the present invention may include diagnostic reagents and nutrients as active substances. The active substances that may be used in the pharmaceutical composition of the present invention are not limited to those mentioned above.

The composition and the dosage form of this invention is not limited to the above mention embodiments, and modification may be made thereto by a person skilled in the art. The invention may be explained by the representative examples, which are provided only for the purpose of illustrating certain aspects of the present invention. Therefore, they are not to be construed as limiting the scope of the present invention in any way.

EXAMPLES

<Example 1> Preparation of Film Made of the Composition

Pectin and guar gum (4:1 w/w) were mixed and dissolved in distilled water to a final concentration of 2% (w/v). The pH of aliquots of the mixture was adjusted to pH 4, 5, 6, 7, 8, and 10 with $Na_2CO_3$. Film with a thickness of 150 $\mu$m were cast on a Teflon plate with each aliquot.

Additional samples were also prepared wherein locust bean gum was added in place of guar gum, and the pH of these samples was adjusted to pH 4 and pH 8. Films were cast and dried. The thickness of these dried films was 150 $\mu$m.

Further, other samples were prepared wherein pectin was dissolved in distilled water, and the pH was adjusted to pH 4 and pH 8 with $Na_2CO_3$. These samples were also cast as films and dried. The thickness of these dried films was also 150 $\mu$m.

Finally, films of guar gum and of locust bean gum were prepared at pH 7 and pH 14 as described above. Thickness of these dried films was also 150 $\mu$m.

All prepared films were cut into pieces with a dimension of 1 cm×1 cm.

Samples were weighed and subjected to a dissolution test. The medium used for testing solubility was simulated intestinal fluid (SIF). After 6 hours in SIF, samples were withdrawn from the medium, washed, and dried. The dried samples were then weighed and compared with pre-test weights.

The results of this experiment are presented in Table 1 (n=3):

TABLE 1

| Film | % Remaining after 6 hrs |
|---|---|
| Pectin/guar gum, pH 4 | 0 |
| Pectin/guar gum, pH 5 | 0 |
| Pectin/guar gum, pH 6 | 16 ± 3 |
| Pectin/guar gum, pH 7 | 61 ± 3 |
| Pectin/guar gum, pH 8 | 70 ± 4 |
| Pectin/guar gum, pH 10 | 71 ± 3 |
| Pectin/locust bean gum, pH 4 | 0 |
| Pectin/locust bean gum, pH 8 | 62 ± 5 |
| Pectin, pH 4 | 0 |
| Pectin, pH 8 | 0 |
| Guar gum, pH 7 | 0 |
| Guar gum, pH 14 | 0 |
| Locust bean gum, pH 7 | 0 |
| Locust bean gum, pH 14 | 0 |

From Table 1, it can be seen that the films prepared at pH 7 and above with the mixtures of pectin and guar gum or pectin and locust bean gum were not readily dissolved in the simulated intestinal fluid (SIF). Films of the same mixtures prepared at below pH 7 and films of only one of the polysaccharides, regardless of pH, were easily dissolved. Therefore, the composition for colonic drug delivery of this invention requires a mixture of at least two polysaccharides, e.g. pectin and galactomannan, prepared at an environmental pH of about 7 or greater.

<Example 2> Measurement of Tensile Strength

Films were made according to the procedure of Example 1 of a mixture of pectin and guar gum (4:1 w/w) prepared at either pH 4 or pH 8. These films were cut to a dimension of 1×7 cm. Then, the films were tested in an Instron Tensile Strength Machine to measure the tensile strength. The results are presented in Table 2 (n=6):

TABLE 2

| Film | Breaking Load (g) | Strain at Maximum (%) |
|---|---|---|
| Pectin/guar gum, pH 4 | 130.5 ± 12.1 | 60.93 ± 10 |
| Pectin/guar gum, pH 8 | 395.6 ± 16 | 115.7 ± 8.5 |

These results show that the films prepared at an environmental pH of about 7 or above have superior tensile properties as compared to films prepared at a pH below 7.

<Example 3> Coating of Tablets with the Composition

Tablets containing 100 mg of ibuprofen as a model drug were coated with the composition prepared according to the procedure of Example 1. The weight ratio of pectin to guar gum was 4:1, and the pH was adjusted to pH 8. The coating was processed with a Hi-Coater (HCT-MINI, Freund Ind., Japan), and the coatings were prepared to reach amounts of 8 mg/cm$^2$, 15 mg/cm$^2$, 26 mg/cm$^2$, and 35 mg/cm$^2$.

Additional tablets containing 100 mg of ibuprofen as a model drug were coated with composition prepared according to the procedure of Example 1 wherein locust bean gum was added in place of guar gum. The weight ratio of pectin to locust bean gum was 4:1, and the pH was adjusted to pH 8. The coating was processed with a Hi-Coater (HCT-MINI, Freund Ind., Japan), and the coating were prepared to reach amount of 15 mg/cm$^2$.

Control tablets containing 100 mg of ibuprofen as a model drug were coated by three other compositions. Each of those composition was composed of pectin and guar gum (4:1 weight ratio) at a pH of 4, pectin and locust bean gum (4:1 weight ratio) at a pH of 4, and pectin of the same concentration at a pH of 8. Coating thickness was 15 mg/cm².

A disintegration test was performed in simulated gastric fluid (SGF), simulated intestinal fluid (SIF) for 24 hours with a disintegration tester DT-400, Fine Scientific Instrument, Korea). SGF and SIF were prepared according to the United States Pharmacopoeia, relevant parts of which are hereby incorporated by reference and which is summarized herein. SCF was 50 mM phosphate buffer, 26 pg/ml Pectinex Ultra SPL(Novo Nordisk), and 20 unit/ml galactomannanase (Novo Nordisk).

In addition, disintegration was tested in a fecal solution prepared by a modification of the method of Macfarlane et al., 60 J. Appl. Bacteriol. 195(1986), hereby incorporated by reference.

All disintegration test results are presented in Table 3, expressed as disintegration time.

TABLE 3

| Coating | SGF | SIF | SCF | Fecal Sol. |
|---|---|---|---|---|
| Pectin/guar gum 8 mg/cm² | ND[a] | ND | 45 min | 75 min |
| Pectin/guar gum 15 mg/cm² | ND | ND | 60 min | 120 min |
| Pectin/guar gum 26 mg/cm² | ND | ND | 150 min | 190 min |
| Pectin/guar gum 35 mg/cm² | ND | ND | 470 min | 510 min |
| Pectin/guar gum pH 4, 15 mg/cm² | 120 min | 60 min | 30 min | —[b] |
| Pectin/locust bean gum, pH 8 15 mg/cm² | ND | ND | 60 min | 120 min |
| Pectin/locust bean gum, pH 4 15 mg/cm² | 120 min | 60 min | 30 min | — |
| Pectin | 120 min | 30 min | 21 min | — |

[a]Not disintegrated during 24 hours
[b]Not determined

<Example 4> Drug Release Test

Figure 1:
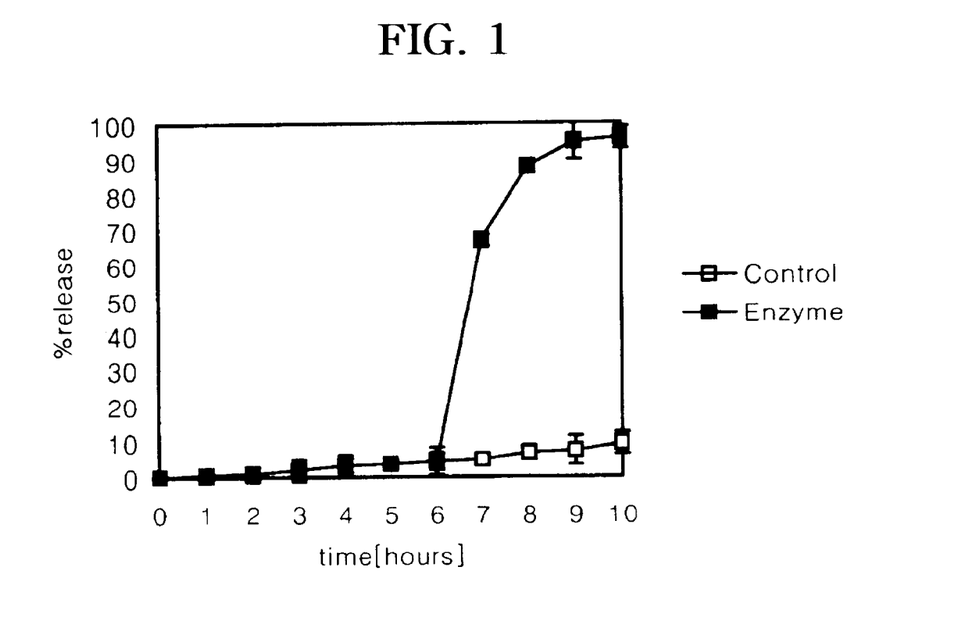
FIG. 1 shows the results of a drug release wherein ibuprofen tablets coated with a composition according to the present invention comprising 15 mg/cm$^2$ of a 4:1 weight ratio of pectin: guar gum were incubated successively for 2 hours in simulated gastric fluid (SGF), 4 hours in simulated intestinal fluid (SIF), and 4 hours in either simulated colonic fluid (SCF;■) or buffer (□)

A drug release test was performed with tablets coated with the composition according to the present invention. These tablets were prepared by the procedure of Example 3, with a coating of 15 mg/cm². The tablets were incubated successively for 2 hours in SGF, 4 hours in SIF, and 4 hours in either SCF or 50 mM phosphate buffer. Released ibuprofen was measured every hour by HPLC (HP-1100, Hewlett-Packard, Column: μBondapak C-18). The results are illustrated in FIG. 1.

The minimal drug was released in SGF and SIF. In addition, very little drug was released in the control buffer (SCF without enzymes), whereas the entire amount of drug was release in SCF within 1 or 2 hours. The data obtained in the drug release test show that the composition can protect the loaded drug from being released in the upper GI tract, and the release of drug is dependent only on colonic enzymes and is independent of pH and transit time.

<Example 5> Variation of the Ratio of the Composition

Tablets containing 100 mg ibuprofen as a model drug were coated by the composition prepared according to the procedure of Example 3. The ratio of pectin and guar gum were 4:1, 4:1.5 and 4:2. The pH of all formulations was adjusted to 8. The coating was processed with the Hi-Coater (HCT-MINI, Freund Ind., Japan) to reach an amount of 15 mg/cm².

Disintegration was performed in simulated gastric fluid (SGF), simulated intestinal fluid (SIF), and simulated colonic fluid (SCF) for 24 hours with the disintegration tester DT 400, Fine Scientific Instrument, Korea). SGF and SIF were prepared as described above, i.e. according to USP.SCF contained 50 mM phosphate buffer with 26 pg/ml Pectinex Ultra SPL (Novo Nordisk) and 20 unit/ml galactomannanase (ovo Nordisk) was used as SCF.

Also, instead of SCF, the fecal solution was used as the medium for the disintegration test. The fecal solution was prepared by a modification of the method of Macfarlane, et al., in J. Appl. Bacteriol., 60, p. 195(1986). All disintegration test results are presented in Table 4, expressed by disintegration time.

TABLE 4

| Coating | SGF | SIF | SCF | Fecal |
|---|---|---|---|---|
| Pectin:guar gum 4:1 | ND[a] | ND | 60 min | 120 min |
| Pectin:guar gum 4:1.5 | ND | ND | 180 min | 270 min |
| Pectin:guar gum 4:2 | ND | ND | 485 min | 495 min |

[a]Not disintegrated during 24 hours.

It is clearly presented that variation in the ratio of the composition can delay the degradation time in the colon, thus controlling the release of drugs selectively in the ascending, transverse or descending colon.

<Example 6> Coating of the Soft Capsules and Hard Capsules

Soft capsules filled with mineral oil and hard capsules filled with budesonide pellets were coated with the composition of the present invention according to the procedure of Example 3. The ratio of pectin to guar gum was 4:1 and the pH was adjusted to 8. The coating was applied at 15 mg/cm².

Coated capsules were subjected to the disintegration test under the conditions described as above. Also, a fecal disintegration test was performed under the conditions described above. The results are presented in Table 5 in terms of disintegration time.

TABLE 5

| | SGF | SIF | SCF | Fecal |
|---|---|---|---|---|
| Soft Capsule | ND[a] | ND | 60 min | 120 min |
| Hard Capsule | ND | ND | 60 min | 120 min |

[a]Not disintegrated during 24 hours

<Example 7> Coating of the pellets

Figure 2:
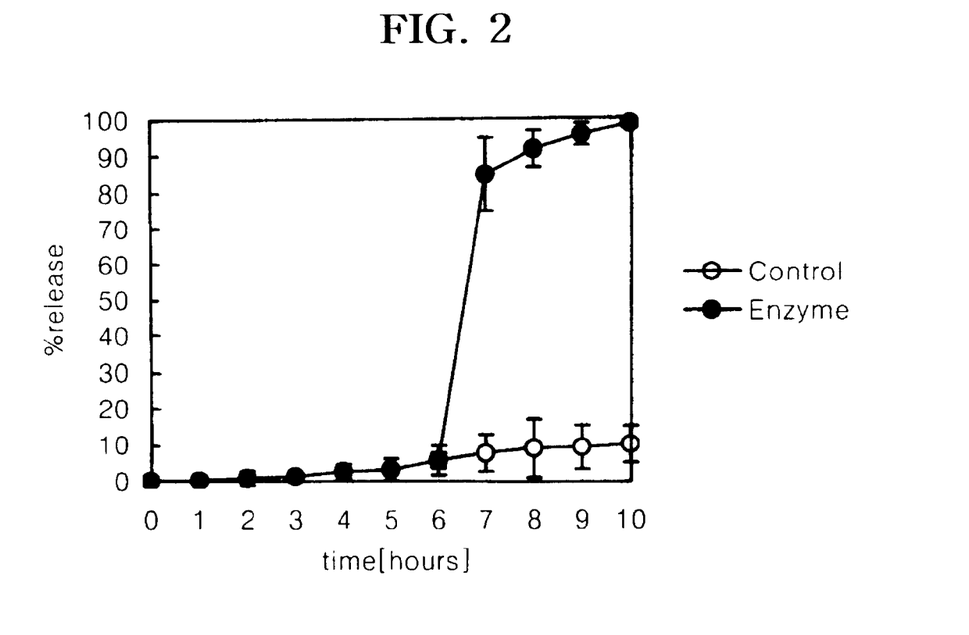
FIG. 2 shows the results of a drug release wherein budesonide pellets coated with a 100 μm film of 4:1 weight ratio of pectin: guar gum according to the present invention were incubated successively for 2 hours in SGF, 4 hours in SIF, and 4 hours in either SCF (○) or buffer(○).

Pellets containing budesonide were prepared with a Fluid-Bed Granulator (GPCG-I, Glatt). Pellets were then coated with the composition according to the present invention using the Flow-Coater. Thickness of the coated film was about 100 μm. The gelatin hard capsules were filled with the coated pellets and subjected to a drug release test. The test was performed by incubating the dosage form in SGF for 2 hours, followed by incubation in SIF for 4 hours and then SCF for 4 hours. As a control, during the SCF incubation, half of the samples under the drug release test were incubated in SCF without Pectinex and galactomannanase, that is, in buffer. Released budesonide was measured every hour by HPLC (HP-1100, Hewlett-Packard, Column: μBondapak C-18). The results are similar to those of the coated tablets and are illustrated in FIG. 2.

The results show that there was minimal release in the SGF and the SIF medium. In addition, in the SCF buffer without enzymes (control), the drug released was minimal also. In SCF, however, the drug was completely released within about 1 or 2 hours. These results show that the composition can protect the loaded drug from being released in the upper GI tract and that its release is dependent only on specific colonic enzymes. Further, release is independent of the pH or transit time, which is true for both coated tablets and pellets.

<Example 8> Manufacture of hard capsules

Hard capsules were manufactured with a conventional pin molder. Thickness was about 100 mm. The hard capsules were filled with pellets containing budesonide (non coated) and were subjected to the disintegration test according to the procedure of Example 7. The results were substantially similar to those of coated tablets. No disintegration was detected in either SGF or SIF. Complete disintegration occurred in 75 min in SCF and in 132 min in fecal solution. These results show that the composition according to the present invention can be applied advantageously to the shell material of hard capsules.

<Example 9> Preparation of Matrix Pellets

Figure 3:
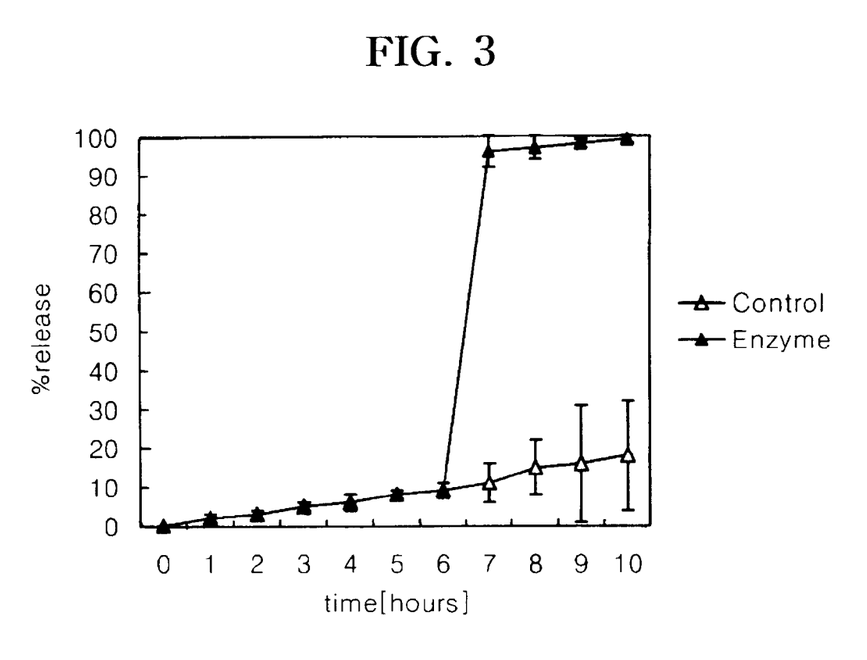
FIG. 3 shows the results of a drug release wherein sugar seeds coated with a 100 μm film comprising a mixture of diclofenac sodium and a 4:1 weight ratio of pectin: guar gum according to the present invention were incubated successively for 2 hours in SGF, 4 hours in SIF, and 4 hours in either SCF (Δ) or buffer (Δ).

Matrix pellets containing diclofenac sodium were prepared using a Fluid-Bed Granulator (GPCG-I, Glatt). Nonpareil sugar seeds were coated with a mixture of the composition according to the present invention and the drug. The prepared pellets were subjected to the drug release test according to the procedure of Example 4. Results were similar to those obtained with ibuprofen and budesonide and are illustrated in FIG. 3.

As described above, the composition and the pharmaceutical dosage form of the present invention, which comprises a polysaccharide, preferably pectin, and galactomannan, were prepared at an environmental pH of about 7 or greater. The composition is not degraded or disintegrated in the upper gastrointestinal tract, but is degraded effectively in the colon by colonic bacterial enzymes, thereby rendering the active substance contained in the composition to be delivered selectively to the colon. The drug targeting site in the colon can be selected simply by adjusting the ratio of galactomannan to pectin in the composition, or by adjusting the size of the dosage form of the composition. Since each component of the composition is degradable only by colonic enzymes, a burst of drug release in the colon can be achieved due to the synergistic effect of the enzymatic reaction. In addition, the degradation of the composition does not depend on the transit time or the pH of the upper GI tract, thus rendering the drugs to be delivered specifically and efficiently to the colon.

While the invention has been described with respect to certain specific embodiments, it should be recognized that various modifications and changes may be made by those skilled in the art, which modifications also fall within the scope of the invention as defined by the appended claims.

What is claimed is:

1. A pharmaceutical composition comprising an effective amount of a drug, diagnostic reagent, or mixture thereof, and a polysaccharide mixture formed in an aqueous medium at a pH of about 7 or above of (a) a polysaccharide selected from the group consisting of pectin, derivatives of pectin, and mixture thereof, and (b) galactomannan, without use of a cross-linking agent, wherein the drug is an antiinfective, analgesic, anotexic, helminthic, antiarthritic, antiasthmatic, anticonvulsant, antidepressant, antidiabetic, antidiarrheal, antihistamine, antiinflammatory, antimigraine, antinauseant, antineoplastic, antiparkinsonism, antipruritic, antipsychotic, antipyretic, antispasmodic, anticholinergic, sympathomimetic, xanthine derivative, potassium channel blocker, calcium channel blocker, beta-blocker, alpha-blocker, antiarrhythmic, antihypertensive, diuretic, antidiuretic, vasodilator, central nervous system stimulant, vasoconstrictor, decongestant, hormone, hypnotic, immunosuppressive, muscle relaxant, parasympatholytic, psychostimulant, sedative, tranquilizer, or a combination thereof.

2. The composition of claim 1 wherein said polysaccharide is pectin.

3. The composition of claim 1 wherein the weight ratio of polysaccharide:galactomannan is from about 50:50 to about 99.9:0.1.

4. The composition of claim 3 wherein the weight ratio of polysaccharide:galactomannan is from about 66.6:33.4 to about 90:10.

5. A pharmaceutical composition comprising an effective amount of a drug, diagnostic reagent, or mixture thereof in contact with a composition consisting essentially of a polysaccharide mixture formed in an aqueous medium at a pH of about 7 or above of (a) a polysaccharide selected form the group consisting of pectin, derivatives of pectin, and mixtures thereof, and (b) galactomannan, without use of a cross-linking agent, wherein the drug is an antiinfective, analgesic, anorexic, helminthic, antiarthritic, antiasthmatic, anticonvulsant, antidepressant, antidiabetic, antidiarrheal, antihistamine, antiinflammatory, antimigraine, antinauseant, antineoplastic, antiparkinsonism, antipruritic, antipsychotic, antipyretic, antispasmodic, anticholinergic, sympathomimetic, xanthine derivative, potassium channel blocker, calcium channel blocker, beta-blocker, alpha-blocker, antiarrhythmic, antihypertensive, diuretic, antidiuretic, vasodilator, central nervous system stimulant, vasoconstrictor, decongestant, hormone, hypnotic, immunosuppressive, muscle relaxant, parasympatholytic, psychostimulant, sedative, tranquilizer, or a combination thereof.

6. The pharmaceutical composition of claim 5 wherein said polysaccharide is pectin.

7. The pharmaceutical composition of claim 5 wherein the weight ratio of polysaccharide:galactomannan is from about 50:50 to about 99.9:0.1.

8. The pharmaceutical composition of claim 7 wherein the weight ratio of polysaccharide:galactomannan is from about 66.6:33.4 to about 90:10.

9. The pharmaceutical composition of claim 5 wherein said drug is a member selected from the group consisting of mesalamine, balsalazide, olsalazine, ibuprofen, prednisolone, dexamethasone, budesonide, beclomethasone, flucticasone, tioxocortal, hydrocortisone, metronidazole, cyclosporin, methotrexate, domperidone, 5-fluorouracil, bisacodyl, senna, insulin, vasopressin, growth hormones, colony stimulating factors, calcitonin, immunoglobulin, glibenclimide, diltiazem, verapamil, nifedipine, captopril, benazepril, enalapril, theophylline, naxopren, diclofenac, acyclovir, omeprazole, lovastatin, alendronate, desmopressin, metformin, metoprolol, cisapride, tacrine, mixtures thereof and probiotics.

10. The pharmaceutical composition of claim 5 wherein said drug, diagnostic reagent, of mixture thereof is in the form of a tablet, a pill, a seed, or a capsule formulation and is coated with said polysaccharide mixture to form a coated formulation.

11. The pharmaceutical composition of claim 10 wherein said coating is 1–100 mg/cm² in size.

12. The pharmaceutical composition of claim 11 wherein said coating is 1–40 mg/cm² in size.

13. The pharmaceutical composition of claim 10 wherein the weight ratio of polysaccharide:galactomannan of said polysaccharide mixture is from about 66.6:33.4 to about 90:10.

14. The pharmaceutical composition of claim 5 wherein said drug, diagnostic reagent, or mixture thereof is admixed with said polysaccharide mixture to form a matrix formation.

15. The pharmaceutical composition of claim 5 wherein said drug, diagnostic reagent, or mixture thereof is encapsulated with a shell composed of said polysaccharide mixture to form a hard capsule formulation.

16. The pharmaceutical composition of claim 15 wherein said shell is 1–100 μm in thickness.

17. The pharmaceutical composition of claim 16 wherein said shell is 1–40 μm in thickness.

18. A method for preparing a colon selective pharmaceutical composition for oral delivery of a drug, diagnostic reagent, or mixture thereof comprising forming a polysaccharide mixture in an aqueous medium at a pH of about 7 or above of (a) a polysaccharide selected from the group consisting of pectin, derivatives of pectin, and mixtures thereof, and (b) galactomannan, without use of a cross-linking agent, and contacting the polysaccharide mixture with a drug, diagnostic regent or mixture thereof.

19. The method of claim 18 wherein the weight ratio of polysaccharide:galactomannan is from about 50:50 to about 99.9:0.01.

20. The method of claim 19 wherein the weight ratio of polysaccharide:galactomannan is from about 66.6:33.4 to about 90:10.

21. The method of claim 18, wherein the polysaccharide mixture forms a coating, capsule shell, or matrix.

22. The method of claim 21 wherein said polysaccharide mixture is a coating 1–100 mg/² in size.

23. The method of claim 22 wherein said polysaccharide mixture is a coating 1–40 mg/cm² in size.

24. The method of claim 21 wherein said polysaccharide mixture is a capsule shell 1–100 μm in size.

25. The method of claim 24 wherein said polysaccharide mixture is a capsule shell 1–40 μm in size.

26. A method of delivering a drug, nutrient, diagnostic reagent, or mixture thereof to the colon of a subject, without substantial release into the upper gastrointestinal tract, comprising orally administering a composition comprising said drug, nutrient, diagnostic reagent or mixture thereof to the subject and a polysaccharide mixture formed in an aqueous medium at a pH of about 7 or above of (a) a polysaccharide selected from the group consisting of pectin, derivative of pectin, and mixtures thereof, and (b) galactomannan, without use of a cross-linking agent, wherein the drug, nutrient, diagnostic reagent or mixture thereof is released into the colon of the subject without substantial release into the upper gastrointestinal tract.

27. The method of claim 26 wherein said polysaccharide is pectin.

28. The method of claim 26 wherein the weight ratio of polysaccharide:galactomannan is from about 50:50 to about 99.9:0.1.

29. The method of claim 26 wherein the weight ratio of polysaccharide:galactomannan is from about 66.6:33.4 to about 90.10.

30. The method of claim 26 wherein said drug, diagnostic reagent or mixture thereof is in the form of a tablet, a pill, a seed, or a capsule formulation and is coated with said polysaccharide mixture to form a coated formulation.

31. The method of claim 26 wherein said drug, diagnostic reagent or mixture thereof is admixed with said polysaccharide mixture to form a matrix formulation.

32. The method of claim 26 wherein said drug, diagnostic reagent or mixture thereof is encapsulated with a shell composed of said polysaccharide mixture to form a hard capsule formulation.

\* \* \* \* \*

UNITED STATES PATENT AND TRADEMARK OFFICE
CERTIFICATE OF CORRECTION

| | |
|---|---|
| PATENT NO. | : 6,413,494 B1 |
| DATED | : July 2, 2002 |
| INVENTOR(S) | : Seung Seo Lee, Chang Baeg Lim, Chaul Min Pai, Sujung Lee, In Park, Gun Seomoon and Heenam Park |

It is certified that error appears in the above-identified patent and that said Letters Patent is hereby corrected as shown below:

<u>Title page,</u>
Item [75], Inventors: "Moon Gun Seo" should read -- Gun Seomoon --.

Signed and Sealed this

Twenty-sixth Day of November, 2002

Attest:

Attesting Officer

JAMES E. ROGAN
*Director of the United States Patent and Trademark Office*